(12) United States Patent
Ogihara et al.

(10) Patent No.: US 10,307,358 B2
(45) Date of Patent: Jun. 4, 2019

(54) ORAL COMPOSITION

(71) Applicant: Kao Corporation, Chuo-ku, Tokyo (JP)

(72) Inventors: Aya Ogihara, Tokyo (JP); Morihide Itano, Koshigaya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/108,445

(22) PCT Filed: Dec. 27, 2013

(86) PCT No.: PCT/JP2013/085242
§ 371 (c)(1),
(2) Date: Jun. 27, 2016

(87) PCT Pub. No.: WO2015/097899
PCT Pub. Date: Jul. 2, 2015

(65) Prior Publication Data
US 2016/0324748 A1    Nov. 10, 2016

(51) Int. Cl.
| | |
|---|---|
| *A61Q 11/00* | (2006.01) |
| *A61K 8/60* | (2006.01) |
| *A61K 8/41* | (2006.01) |
| *A61K 8/43* | (2006.01) |
| *A61K 8/49* | (2006.01) |
| *A61K 8/92* | (2006.01) |
| *C07H 15/04* | (2006.01) |
| *A61K 9/00* | (2006.01) |
| *A61K 47/10* | (2017.01) |
| *A61K 47/14* | (2017.01) |
| *A61K 47/18* | (2017.01) |
| *A61K 47/26* | (2006.01) |
| *A61K 47/32* | (2006.01) |
| *A61K 9/08* | (2006.01) |
| *A61K 47/44* | (2017.01) |
| *A61K 31/4425* | (2006.01) |
| *A61K 31/7028* | (2006.01) |

(52) U.S. Cl.
CPC ............ *A61K 8/604* (2013.01); *A61K 8/416* (2013.01); *A61K 8/43* (2013.01); *A61K 8/4926* (2013.01); *A61K 8/60* (2013.01); *A61K 8/922* (2013.01); *A61K 9/0053* (2013.01); *A61K 9/08* (2013.01); *A61K 31/4425* (2013.01); *A61K 31/7028* (2013.01); *A61K 47/10* (2013.01); *A61K 47/14* (2013.01); *A61K 47/186* (2013.01); *A61K 47/26* (2013.01); *A61K 47/32* (2013.01); *A61K 47/44* (2013.01); *A61Q 11/00* (2013.01); *C07H 15/04* (2013.01); *A61K 2800/592* (2013.01)

(58) Field of Classification Search
CPC ...... A61K 8/604; A61K 8/416; A61K 8/4926; A61K 8/922; A61K 8/60; A61K 8/43; A61K 2800/592; A61Q 11/00; C07H 15/04

USPC .................................................... 424/49, 401
See application file for complete search history.

(56) References Cited

U.S. PATENT DOCUMENTS

| | | | |
|---|---|---|---|
| 5,409,902 | A | 4/1995 | Carson et al. |
| 5,624,906 | A | 4/1997 | Vermeer |
| 6,117,417 | A | 9/2000 | Wicks et al. |
| 8,834,852 | B2 | 9/2014 | Itano et al. |
| 2008/0255058 | A1 | 10/2008 | Itano et al. |
| 2010/0215592 | A1 | 8/2010 | Itano et al. |
| 2010/0330005 | A1 | 12/2010 | Yoshida et al. |
| 2012/0269741 | A1 | 10/2012 | Yano et al. |

FOREIGN PATENT DOCUMENTS

| | | |
|---|---|---|
| CN | 101027034 A | 8/2007 |
| CN | 101909589 A | 12/2010 |
| EA | 001234 B1 | 12/2000 |
| GB | 2 038 182 A | 7/1980 |
| JP | 06-080545 A | 3/1994 |
| JP | 2002-179541 A | 6/2002 |
| JP | 2006-124384 A | 5/2006 |
| JP | 2007-291083 A | 11/2007 |
| JP | 2007-291084 A | 11/2007 |

(Continued)

OTHER PUBLICATIONS

International Search Report (ISR) for PCT/JP2013/085242; I.A. fd Dec. 27, 2013, dated Mar. 18, 2014, from the Japanese Patent Office, Tokyo, Japan.

(Continued)

*Primary Examiner* — Lezah Roberts
(74) *Attorney, Agent, or Firm* — Sterne, Kessler, Goldstein & Fox P.L.L.C.

(57) ABSTRACT

The present invention relates to an oral composition having an enhanced solubility of an alkyl galactoside while holding an inhibiting effect on coaggregation of the alkyl galactoside well.

The present invention provides an oral composition comprising the following components: (A) 0.001 mass % or more and 1 mass % or less of a compound represented by the following formula (I):

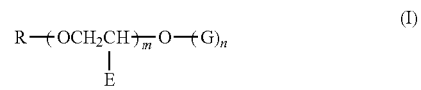

wherein R is an optionally substituted linear or branched alkyl group having 8 to 18 carbon atoms, G is a galactose residue, E is a hydrogen atom or a methyl group, m is an integer of 0 to 200, and n is an integer of 1 to 30; (B) 0.001 mass % or more and 0.1 mass % or less of a cationic bactericide; and (C) 35 mass % or more of water.

11 Claims, No Drawings

(56) References Cited

FOREIGN PATENT DOCUMENTS

| JP | 2007-291085 A | 11/2007 |
|---|---|---|
| JP | 2011-162524 A | 8/2011 |
| WO | WO 2006-035821 A1 | 4/2006 |
| WO | WO 2007/066497 A1 | 6/2007 |

OTHER PUBLICATIONS

International Preliminary Report on Patentability (IPRP), Chapter I of the Patent Cooperation Treaty, including the Written Opinion for PCT/JP2013/085242; I.A. fd Dec. 27, 2013, dated Jun. 28, 2016, by the International Bureau of WIPO, Geneva, Switzerland.
Takemoto, T. et al., "Characteristics of multimodal co-aggregation between *Fusobacterium nucleatum* and streptococci," J Periodontal Res. Jul. 1995;30(4):252-7, Wiley-Blackwell, Malden, MA.
Extended European search report for EP Appl. No. 13900001.2, including the supplementary European search report and the European search opinion, dated Jul. 12, 2017, European Patent Office, Munich, Germany.

ORAL COMPOSITION

FIELD OF THE INVENTION

The present invention relates to an oral composition.

BACKGROUND OF THE INVENTION

Dental caries is, in a sense, an oral infection which is developed by the adherence and colonization of pathogenic bacteria onto the tooth surface. The mechanism for the colonization of oral bacteria on the tooth surface appears to be as follows. First, initial colonizing bacteria such as *Streptococcus oralis, Streptococcus sanguis, Streptococcus gordonii*, and *Actinomyces naeslundii* adsorb onto the enamel surface covered with a thin film (pellicle) of saliva. Then, as these initial colonizing bacteria grow, they coaggregate and start to accumulate plaque. Subsequently, as the plaque matures, the microbial flora shifts from facultative anaerobes to obligate anaerobes, and the obligate anaerobes represented by *Fusobacterium nucleatum* coaggregate with the initial colonizing bacteria. Then, periodontal disease-related bacteria such as *Actinobacillus actinomycetemcomitans, Porphyromonas gingivalis*, and *Prevotella intermedia* further coaggregate with the *Fusobacterium nucleatum* and colonize. Takemoto et al. further suggest that dental caries-related bacteria such as *Streptococcus mutans* and *Streptococcus sobrinus* have the same colonization mechanism because they also coaggregate with *Fusobacterium nucleatum* (Non Patent Literature 1).

As described above, the coaggregation of dental caries pathogens such as *Fusobacteria* and periodontal disease-related bacteria is deeply involved in the generation, development, and progression of dental caries, periodontal disease, halitosis, and the like. As a compound having an effectively inhibiting action on such coaggregation, an alkyl galactoside in which an alkyl group is ether-bonded to galactose is known. In Patent Literature 1, such a compound is used to obtain an oral composition having an inhibiting effect on dental caries and plaque accumulation. Further, in Patent Literature 2, the above alkyl galactoside and a non-ionic bactericide are used in combination to obtain an oral composition that has a coaggregation-inhibiting action on *Fusobacteria* or the like and specifically kills bacteria belonging to the genus *Fusobacterium*.

(Patent Literature 1) JP-A-2006-124384
(Patent Literature 2) JP-A-2007-291083
(Non Patent Literature 1) Journal of Periodontal Research, Vol. 30, p 252-257

SUMMARY OF THE INVENTION

The present invention relates to an oral composition comprising the following components (A), (B), and (C):

(A) 0.001 mass % or more and 1 mass % or less of a compound represented by the following formula (I):

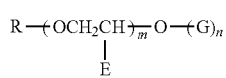

wherein R represents an optionally substituted linear or branched alkyl group having 8 to 18 carbon atoms, G represents a galactose residue, E represents a hydrogen atom or a methyl group, m represents an integer of 0 to 200, and n represents an integer of 1 to 30;

(B) 0.001 mass % or more and 0.1 mass % or less of a cationic bactericide; and (C) 35 mass % or more of water.

An alkyl galactoside is insoluble in water and thus requires an increased content of a surfactant when a preparation containing a large amount of water contains an alkyl galactoside. However, the present inventors revealed that in such a preparation containing an alkyl galactoside and a surfactant in combination, the coaggregation-inhibiting effect of the alkyl galactoside is reduced or inactivated when the surfactant is excessively contained. Further, the present inventors unexpectedly found that a cationic bactericide greatly contributes to enhancement of the solubility of an alkyl galactoside, along with further associated effects to be expected.

Thus, the present inventors unexpectedly found that, when an oral composition contains a specific alkyl galactoside that is normally insoluble in water, and a predetermined amount of a cationic bactericide in combination, the solubility in water can be enhanced effectively.

According to the oral composition of the present invention, the solubility of an alkyl galactoside in water can be enhanced effectively without increasing the content of a surfactant, and thus the alkyl galactoside can be dissolved well even in a composition containing a large amount of water. For this reason, the coaggregation-inhibiting effect of an alkyl galactoside on *Fusobacteria* and the like can be held well and further the adsorption of a cationic bactericide onto teeth can be effectively increased to fully exhibit the bactericidal effect thereof. Accordingly, when the oral composition of the present invention is used, outstanding effects of inhibiting plaque accumulation and inhibiting halitosis can also be achieved.

DETAILED DESCRIPTION OF THE INVENTION

The present invention will be described below in detail.

The oral composition of the present invention comprises, as the component (A), 0.001 mass % or more and 1 mass % or less of a compound represented by the following formula (I):

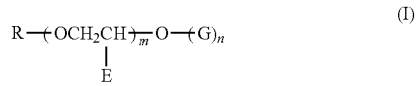

wherein R represents an optionally substituted linear or branched alkyl group having 8 to 18 carbon atoms, G represents a galactose residue, E represents a hydrogen atom or a methyl group, m represents an integer of 0 to 200, and n represents an integer of 1 to 30.

The compound represented by the formula (I) of the component (A) is a compound in which one or more galactose residues are ester-bonded to the alkyl group R having 8 to 18 carbon atoms at the α-position or β-position directly or via one or more oxyethylene groups or oxypropylene groups. R in the formula (I) may be linear or branched and specific examples thereof include an n-octyl group, an n-decyl group, an n-undecyl group, an n-dodecyl group, an n-tetradecyl group, an n-hexadecyl group, an n-octadecyl group, a 2-ethyl hexyl group, an isodecyl group, a lauryl group, and an isostearyl group (isooctadecyl group).

R in the formula (I) has preferably 10 to 18 carbon atoms, more preferably 10 to 16 carbon atoms, even more preferably 10 to 14 carbon atoms, from the perspective of enhancing the solubility of the component (A) by the component (B) to be described later, from the perspectives of the coaggregation-inhibiting effect, the retention properties in the oral cavity, and the like, and from the perspective of increasing the adsorption of the cationic bactericide onto teeth.

One or more hydrogen atoms of R may be replaced with a substituent, and examples of the substituent include an alkoxy group having 1 to 6 carbon atoms, a halogen atom (e.g., fluorine, chlorine, bromine, or iodine), a nitro group, a haloalkyl group having 1 to 6 carbon atoms, and a haloalkoxy group having 1 to 6 carbon atoms. The galactose in the compound represented by the formula (I) used in the present invention encompasses all of a pyranose form, a furanose form, and a mixture thereof. m in the formula (I) represents the degree of polymerization of oxyethylene groups or oxypropylene groups, and is an integer of 0 to 200, preferably 0 to 12, more preferably 0 to 3, even more preferably 0, from the perspective of the coaggregation-inhibiting effect. n in the formula (I) represents the degree of condensation of galactose, is an integer of 1 to 30, preferably 1 to 6, more preferably 1 to 3, from the perspective of the foaming properties.

E in the formula (I) is preferably a hydrogen atom from the perspective of the coaggregation-inhibiting effect.

As the component (A), a mixture containing two compounds represented by the formula (I) may be used. In this case, R in the formula (I) as the component (A) in the composition is an alkyl group having an average number of carbon atoms of 8 to 18, and from the perspective of enhancing the solubility of the component (A) by the component (B) to be described later, from the perspective of the coaggregation-inhibiting effect, the retention properties in the oral cavity, and the like, and from the perspective of increasing the adsorption of the cationic bactericide onto teeth, the average number of carbon atoms in R in the formula (I) is preferably 10 to 18 carbon atoms, more preferably 10 to 16 carbon atoms, even more preferably 10 to 14 carbon atoms. Specifically, one or more selected from the group consisting of a lauryl group, an n-octyl group, an n-decyl group, and an isodecyl group are preferable. The average degree of polymerization, x, of the degree of polymerization, m, of oxyethylene groups or oxypropylene groups in the component (A) in the composition is a number of 0 to 200, preferably a number of 0 to 12, more preferably a number of 0 to 3, even more preferably 0 to 1. The average degree of condensation, y, of the degree of condensation, n, of galactose in the component (A) in the composition is a number of 1 to 30, preferably a number of 1 to 6, more preferably a number of 1 to 3, from the perspective of the coaggregation-inhibiting effect. Note that the average degree of condensation, y, of galactose can be calculated based on the component composition of each degree of condensation obtained by an analysis method such as gel permeation chromatography. For example, in the case of an alkyl galactoside mixture having a degree of condensation of galactose of 1 to z, when a molar ratio of galactoside having a degree of condensation of z is $a_z$ ($a_1+a_2+a_3+\ldots+a_z=1$), the average degree of condensation, y, of galactose is expressed as $y=a_1 \times 1+a_2 \times 2+\ldots+a_z \times z=\Sigma(a_z \times z)$.

In addition, the average degree of polymerization, x, of oxyethylene groups or oxypropylene groups and the average number of carbon atoms of the alkyl group represented by R can be calculated in the same manner.

The compound represented by the formula (I) as the above component (A) can be produced by the method of Hori et al. (Journal of the Pharmaceutical Society of Japan, Vol. 79, No. 1, p 80-83) or Production Examples 1 and 2 to be described later.

The compound represented by the formula (I) of the component (A) strongly inhibits the coaggregation of bacteria belonging to the genus *Fusobacterium*, which are normal bacteria, and dental caries pathogens. Examples of the bacteria belonging to the genus *Fusobacterium* used herein include *Fusobacterium nucleatum* and *Fusobacterium russii*. Examples of the dental caries pathogens include *Streptococcus mutans* and *Streptococcus sobrinus*. The conventionally known sugar esters of fatty acids is decomposed in the oral cavity to produce acids which cause dental caries, but the compound represented by the formula (I) of the component (A) is not decomposed in the oral cavity to produce acids which cause dental caries. Consequently, the component (A) of the present invention effectively exhibits the coaggregation-inhibiting effect, and thus the composition comprising the component (A) of the present invention can also function as a dental caries-inhibiting agent or a dental caries-preventing agent.

The content of the component (A) in the oral composition of the present invention is 0.001 mass % or more, preferably 0.01 mass % or more, more preferably 0.02 mass % or more, from the perspective of being dissolved well in water of the component (C) to be described later and fully exhibiting the coaggregation-inhibiting effect, and from the perspective of increasing the adsorption of a cationic bactericide of the component (B) onto teeth. The content of the component (A) in the oral composition of the present invention is 1 mass % or less, preferably 0.9 mass % or less, more preferably 0.8 mass % or less, from the perspective of effectively holding the solubility in water of the component (C), and is preferably 0.5 mass % or less, more preferably 0.3 mass % or less, from the perspective of storage stability. Further, the content of component (A) in the oral composition of the present invention is 0.001 mass % or more and 1 mass % or less, preferably 0.01 to 0.9 mass %, more preferably 0.02 to 0.8 mass %, even more preferably 0.02 to 0.5 mass %.

The oral composition of the present invention comprises 0.001 mass % or more and 0.1 mass % or less of a cationic bactericide as the component (B). When the composition comprises the component (B), the component (A) which is normally insoluble in water can be dissolved well in water of the component (C) to be described later. The oral composition contains a large amount of water; however, it, while suppressing an increase in the surfactant content, can effectively prevent the separation and insolubilization of the component (A) in the composition to thereby enhance the homogeneity. As a result, the content of the component (A) can be easily increased to the extent that the coaggregation-inhibiting effect of the component (A) can be fully exhibited while avoiding the reduction or inactivation of the effect. In addition, when the component (A) and the component (B) are used in combination, the absorption of the component (B) onto teeth can also be increased.

Examples of the component (B) include one or more selected from the group consisting of a quaternary ammonium compound and a biguanide compound. Specific examples of the quaternary ammonium compound include cetylpyridinium chloride, benzethonium chloride, benzalkonium chloride, stearyldimethylammonium chloride, stearyltrimethylammonium chloride, cetyltrimethylammonium chloride, methylbenzethonium chloride, lauryltrimethylammonium chloride, and lauroylcolaminoformylmethylpyridinium chloride.

Specific examples of the biguanide compound include chlorhexidine and salts thereof, and examples of the salts include chlorhexidine gluconate and chlorhexidine hydrochloride.

Of these, the component (B) is preferably one or more selected from the group consisting of cetylpyridinium chloride, benzethonium chloride, benzalkonium chloride, chlorhexidine gluconate, and chlorhexidine hydrochloride from the perspective of enhancing the solubility of the component (A), and is more preferably one or more quaternary ammonium compounds selected from the group consisting of cetylpyridinium chloride, benzethonium chloride, and benzalkonium chloride from the perspective of bactericidal performance.

The content of the component (B) in the oral composition of the present invention is 0.001 mass % or more, preferably 0.005 mass % or more, more preferably 0.008 mass % or more from the perspective of enhancing the solubility of the component (A) and from the perspective of bactericidal performance. The content of the component (B) in the oral composition of the present invention is 0.1 mass % or less, preferably 0.08 mass % or less, more preferably 0.06 mass % or less, from the perspective of holding a good flavor and a feeling of use. Further, the content of component (B) in the oral composition of the present invention is 0.001 mass % or more and 0.1 mass % or less, preferably 0.005 to 0.08 mass %, more preferably 0.008 to 0.06 mass %.

The mass ratio of the content of the component (A) to the content of the component (B), (A)/(B), is 0.1 or more, preferably 1 or more, more preferably 2 or more from the perspective of holding the coaggregation-inhibiting effect of the component (A) well and from the perspective of increasing the adsorption of the cationic bactericide onto teeth. The mass ratio of the content of the component (A) to the content of the component (B), (A)/(B), is preferably 100 or less, more preferably 90 or less, even more preferably 80 or less from the perspective of assuring the solubility of the component (A), and is more preferably 40 or less, even more preferably 30 or less from the perspective of storage stability. Further, the mass ratio of the content of the component (A) to the content of the component (B), (A)/(B), is preferably 0.1 or more and 100 or less, more preferably 1 to 90, even more preferably 2 to 80, even more preferably 2 to 40, even more preferably 2 to 30 from the perspective of storage stability.

The oral composition of the present invention comprises 35 mass % or more of water as the component (C). In the present invention, even in the oral composition containing a large amount of water, when the components (A) and (B) are comprised in specific amounts, a good coaggregation-inhibiting effect can be held while enhancing the solubility of the component (A) in water. The content of the component (C) in the oral composition of the present invention is 35 mass % or more, preferably 50 mass % or more, more preferably 60 mass % or more from the perspective of assuring a moderate flowability as a liquid oral composition containing a large amount of water. The content of the component (C) in the oral composition of the present invention is preferably 99.99 mass % or less, more preferably 99.9 mass % or less from the perspective of holding the coaggregation-inhibiting effect well while dissolving the component (A) well. When a nonionic surfactant is contained as the component (D) to be described later, the content of the component (C) is preferably 99.8 mass % or less, more preferably 99.7 mass % or less. When a sugar alcohol to be described later is further contained with the component (D), the content of the component (C) is preferably 95 mass % or less, more preferably 89 mass % or less. Further, the content of the component (C) in the oral composition of the present invention is 35 mass % or more, preferably 35 to 99.99 mass %, more preferably 50 to 99.9 mass %, even more preferably 60 to 99.9 mass %, and when the component (D) is contained, the content of the component (C) is preferably 50 to 99.8 mass %, more preferably 60 to 99.7 mass %. Furthermore, when the component (D) and a sugar alcohol are contained, the content of the component (C) is preferably 50 to 95 mass %, more preferably 60 to 89 mass %.

Note that the content of the component (C) is the balance of the other components in the oral composition of the present invention.

The oral composition of the present invention preferably further contains a nonionic surfactant as the component (D) from the perspective of fully exhibiting the increasing effect on the absorption of the component (B) onto teeth and from the perspective of holding the coaggregation-inhibiting effect of the component (A) well. In the oral composition of the present invention, a specific amount of the component (B) assures a good solubility of the component (A), and at the same time a nonionic surfactant of the component (D) provides the increasing effect on the absorption of the component (B) onto teeth, making it possible to fully exhibit the bactericidal effect of the component (B). In addition, the oral composition requires no increased content of the nonionic surfactant of the component (D) and while effectively containing the component (D) in an amount such that a reduction or in activation of the coaggregation-inhibiting effect of the component (A) is not caused, it can improve the stability of the composition or improve the solubility of an oily component such as a fragrance.

Examples of the component (D) include one or more selected from the group consisting of a polyoxyethylene hydrogenated castor oil, a polyoxyethylene sorbitan fatty acid ester, a polyglycerol fatty acid ester, a polyoxyethylene alkyl ether, an alkyl polyglucoside, and a sucrose fatty acid ester. The average number of moles of ethyleneoxy groups added in a polyoxyethylene hydrogenated castor oil or a polyoxyethylene alkyl ether is preferably 10 to 80, more preferably 30 to 60 from the perspective of assuring the coaggregation-inhibiting effect of the component (A) well. Further, the number of carbon atoms in the fatty acids constituting a polyoxyethylene sorbitan fatty acid ester or a polyglycerol fatty acid ester is preferably 8 to 18, more preferably 10 to 16, even more preferably 10 to 14 from the perspective of a taste and dispersibility or solubility in water and from the perspective of assuring the coaggregation-inhibiting effect of the component (A) well. The number of carbon atoms of the alkyl groups in a polyoxyethylene alkyl ether is preferably 10 to 16, more preferably 10 to 14 from the perspectives of a taste and dispersibility in water and from the perspective of assuring the coaggregation-inhibiting effect of the component (A) well; and the number of carbon atoms of the alkyl groups in an alkyl polyglucoside is preferably 10 to 16, more preferably 10 to 12 from the same perspectives. Further, the number of carbon atoms in the fatty acids constituting a sucrose fatty acid ester is preferably 10 to 16, more preferably 12 to 14, from the perspective of a taste and dispersibility in water and from the perspective of increasing the absorption of the component (B) onto teeth.

Among the component (D), from the perspective of a taste and from the perspective of assuring a good solubility of the component (A) in water and a good adsorption of the component (B) onto teeth, one or more selected from the group consisting of a polyoxyethylene sorbitan fatty acid ester, a polyglycerol fatty acid ester, an alkyl polyglucoside, and a sucrose fatty acid ester are more preferable, and at least one sucrose fatty acid ester is even more preferably contained. From the perspective of assuring a good solubility of the component (A) in water and the coaggregation-inhibiting effect of the component (A), one or more selected from the group consisting of a polyoxyethylene hydrogenated castor oil, a polyoxyethylene sorbitan fatty acid ester, a polyglycerol fatty acid ester, and an alkyl polyglucoside are more preferable.

The content of the component (D) is preferably 0.1 mass % or more, more preferably 0.2 mass % or more from the perspective of holding the solubility of the component (A) in water well and from the perspective of increasing the absorption of the component (B) onto teeth. The content of the component (D) is preferably 1.5 mass % or less, more preferably 1.2 mass % or less, even more preferably 1 mass % or less from the perspective of suppressing reduction or inactivation of the coaggregation-inhibiting effect of the component (A). Further, the content of the component (D) is preferably 0.1 mass % or more and 1.5 mass % or less, more preferably 0.2 to 1.2 mass %, even more preferably 0.2 to 1 mass %.

The mass ratio of the total content of the component (A) and the component (B) to the content of the component (D), {(A)+(B)}/(D), is preferably 0.02 or more and more preferably 0.05 or more from the perspective of assuring a good solubility of the component (A) and the adsorption of the component (B) onto teeth. The mass ratio of the total content of the component (A) and the component (B) to the content of the component (D), {(A)+(B)}/(D), is preferably 2 or less, more preferably 1 or less, even more preferably 0.8 or less, even more preferably 0.6 or less from the perspective of holding a good solubility and the coaggregation-inhibiting effect of the component (A) in a balanced manner. Further, the mass ratio of the total content of the component (A) and the component (B) to the content of the component (D), {(A)+(B)}/(D), is preferably 0.02 or more and 2 or less, more preferably 0.02 to 1, even more preferably 0.05 to 0.8, even more preferably 0.05 to 0.6.

Further, the oral composition of the present invention preferably contains a sugar alcohol from the perspective of effectively increasing the coaggregation-inhibiting effect of the component (A). Sugar alcohols have a retardant action on the bonding of bacteria belonging to the genus *Fusobacterium* and dental caries pathogens and do not produce acids in the oral cavity, and thus may be provide an increasing action on the coaggregation-inhibiting effect. Such sugar alcohols are preferably those having 4 to 12 carbon atoms, and specific examples include one or more selected from the group consisting of sorbitol, mannitol, xylitol, erythritol, reduced palatinose, lactitol, and maltitol. Among these, one or more selected from the group consisting of erythritol, xylitol, maltitol, and reduced palatinose is preferable from the perspective of increasing the coaggregation-inhibiting effect, and sorbitol is preferable from the perspectives of a taste, wettability, and stability.

The content of the sugar alcohol in the oral composition of the present invention is preferably 5 mass % or more, more preferably 8 mass % or more, even more preferably 10 mass % or more from the perspective of effectively increasing the coaggregation-inhibiting effect of the component (A) and from the perspective of achieving a good taste. The content of the sugar alcohol is preferably 30 mass % or less, more preferably 25 mass % or less, even more preferably 20 mass % or less from the perspective of holding a good solubility of the component (A).

The oral composition of the present invention may further contain components other than the above components in a range such that the advantageous effects of the present invention are not inhibited. Examples of such components include a wetting agent, a binder, a teeth quality fortifying agent, a pH regulator, an enzyme, an antiinflammatory agent, a blood circulation improving agent, a preservative, a colorant, a pigment, and a fragrance. Note that preferably an anionic surfactant is not contained unless otherwise inevitably mixed in, or is contained in an amount of more than 0 mass % and 1 mass % or less, and more preferably the anionic surfactant is contained in an amount of 0.7 mass % or less, in the oral composition of the present invention. Preferably an amphoteric surfactant is not contained unless otherwise inevitably mixed in, or is contained in an amount of 1 mass % or less, and more preferably the amphoteric surfactant is contained in an amount of 0.7 mass % or less, in the oral composition of the present invention. Preferably a surfactant other than the component (D), the anionic surfactant, and the amphoteric surfactant is not contained unless otherwise inevitably mixed in, or is contained in an amount of more than 0 mass % and 0.5 mass % or less, and more preferably it is contained in an amount of 0.1 mass % or less, in the oral composition of the present invention from the perspective of suppressing the reduction or inactivation of the coaggregation-inhibiting effect of the component (A). Further, preferably a surfactant other than the component (D), the anionic surfactant, and the amphoteric surfactant is not contained or is contained in an amount of more than 0 mass % and 0.5 mass % or less, and more preferably is contained in an amount of more than 0 mass % or more or 0.1 mass % or less, in the oral composition of the present invention.

Examples of the anionic surfactant include alkyl sulfates, N-acylglutamates, alkyl phosphates, and N-acyl taurine salts, and alkyl phosphates are preferable, and sodium lauryl sulfate is more preferable from the perspectives of a taste, foamability, stability, and the like.

Examples of the amphoteric surfactant include acetic acid betaine, lauryldimethylaminoacetic acid betaine, imidazolinium betaine, 2-alkyl-N-carboxymethyl-N-hydroxyethyl-imidazolium betaine, lauryl sulfobetaine, cocamidopropyl betaine, and N-alkyl-1-hydroxyethylimidazoline betaine sodium.

The oral composition of the present invention may be produced by mixing the above components by a routine method, and is preferably in the form of a liquid oral composition because the oral composition contains a large amount of water as described above. Examples of such a liquid oral composition include mouthwashes, liquid toothpastes, toothwashes, mouth sprays, and gargles. When the oral composition of the present invention is used, the coaggregation-inhibiting effect is fully exhibited and thus plaque accumulation can also be effectively inhibited, and thereby dental caries can also be effectively inhibited and halitosis can also be effectively inhibited. Accordingly, the oral composition of the present invention can effectively act to inhibit plaque accumulation, inhibit or prevent dental caries, and also to inhibit halitosis.

With respect to the embodiments described above, the present invention further discloses the following oral compositions.

[1] An oral composition comprising the following components (A), (B), and (C):

(A) 0.001 mass % or more and 1 mass % or less of a compound represented by the following formula (I):

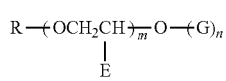

wherein R represents an optionally substituted linear or branched alkyl group having 8 to 18 carbon atoms, G represents a galactose residue, E represents a hydrogen atom or a methyl group, m represents an integer of 0 to 200, and n represents an integer of 1 to 30;

(B) 0.001 mass % or more and 0.1 mass % or less of a cationic bactericide; and (C) 35 mass % or more of water.

[2] The oral composition of the above [1], wherein R in the formula (I) has preferably 10 to 18 carbon atoms, more preferably 10 to 16 carbon atoms, even more preferably 10 to 14 carbon atoms.

[3] The oral composition of the above [1] or [2], wherein m in the formula (I) is preferably 0 to 12, more preferably 0 to 3, even more preferably 0.

[4] The oral composition of the above [1] to [3], wherein n in the formula (I) is preferably 1 to 6, more preferably 1 to 3.

[5] The oral composition of the above [1] to [4], wherein E in the formula (I) is preferably a hydrogen atom.

[6] The oral composition of the above [1] to [5], wherein a content of the component (A) is preferably 0.01 mass % or more, more preferably 0.02 mass % or more, and preferably 0.9 mass % or less, more preferably 0.8 mass % or less, and from the perspective of storage stability, preferably 0.5 mass % or less, more preferably 0.3 mass % or less.

[7] The oral composition of the above [1] to [6], wherein the component (B) is preferably one or more selected from the group consisting of quaternary ammonium compounds and biguanide compounds, more preferably includes cetylpyridinium chloride, benzethonium chloride, benzalkonium chloride, stearyldimethylammonium chloride, stearyltrimethylammonium chloride, cetyltrimethylammonium chloride, methylbenzethonium chloride, lauryltrimethylammonium chloride, lauroylcolaminoformylmethylpyridinium chloride, chlorhexidine, and salts thereof, and the salts include one or more selected from the group consisting of chlorhexidine gluconate and chlorhexidine hydrochloride, is even more preferably one or more selected from the group consisting of cetylpyridinium chloride, benzethonium chloride, benzalkonium chloride, chlorhexidine gluconate, and chlorhexidine hydrochloride, even more preferably one or more quaternary ammonium compounds selected from the group consisting of cetylpyridinium chloride, benzethonium chloride, and benzalkonium chloride.

[8] The oral composition of the above [1] to [7], wherein a content of the component (B) is preferably 0.005 mass % or more, more preferably 0.008 mass % or more, and preferably 0.08 mass % or less, more preferably 0.06 mass % or less.

[9] The oral composition of the above [1] to [8], wherein a mass ratio of a content of the component (A) to a content of the component (B), (A)/(B), is preferably 0.1 or more, more preferably 1 or more, even more preferably 2 or more, and preferably 100 or less, more preferably 90 or less, even more preferably 80 or less, even more preferably 40 or less, even more preferably 30 or less.

[10] The oral composition of the above [1] to [9], wherein a content of the component (C) is preferably 50 mass % or more, more preferably 60 mass % or more, and preferably 99.99 mass % or less, more preferably 99.9 mass % or less, and further when a nonionic surfactant is contained as a component (D), the content of the component (C) is preferably 99.8 mass % or less, more preferably 99.7 mass % less.

[11] The oral composition of the above [1] to [10], wherein the oral composition further comprises 0.1 mass % or more and 1.5 mass % or less of a nonionic surfactant as the component (D), and a content thereof is more preferably 0.2 mass % or more and more preferably 1.2 mass % or less, even more preferably 1 mass % or less.

[12] The oral composition of the above [11], wherein the component (D) is preferably one or more selected from the group consisting of a polyoxyethylene hydrogenated castor oil, a polyoxyethylene sorbitan fatty acid ester, a polyglycerol fatty acid ester, a polyoxyethylene alkyl ether, an alkyl polyglucoside, and a sucrose fatty acid ester, more preferably one or more selected from the group consisting of a polyoxyethylene sorbitan fatty acid ester, polyglycerol fatty acid ester, an alkyl polyglucoside, and a sucrose fatty acid ester, even more preferably includes at least one sucrose fatty acid ester, even more preferably one or more selected from the group consisting of a polyoxyethylene hydrogenated castor oil, a polyoxyethylene sorbitan fatty acid ester, a polyglycerol fatty acid ester, and an alkyl polyglucoside.

[13] The oral composition of the above [11] and [12], wherein a mass ratio of a total content of the components (A) and (B) to a content of the component (D), {(A)+(B)}/(D), is preferably 0.02 or more, more preferably 0.05 or more, and preferably 2 or less, more preferably 1 or less, even more preferably 0.8 or less, even more preferably 0.6 or less.

[14] The oral composition of the above [1] to [13], wherein the oral composition further comprises a sugar alcohol, and a content thereof is preferably 5 mass % or more, more preferably 8 mass % or more, even more preferably 10 mass % or more, and preferably 30 mass % or less, more preferably 25 mass % or less, even more preferably 20 mass % less.

[15] The oral composition of the above [14], wherein the sugar alcohol is preferably one having 4 to 12 carbon atoms, and is one or more selected from the group consisting of sorbitol, mannitol, xylitol, erythritol, reduced palatinose, lactitol, and maltitol, preferably one or more selected from the group consisting of erythritol, xylitol, maltitol, and reduced palatinose, even more preferably sorbitol.

[16] The oral composition of the above [1] to [15], wherein preferably an anionic surfactant is not contained unless otherwise inevitably mixed in, or is contained in an amount of more than 0 mass % and 1 mass % or less, and more preferably the anionic surfactant is contained in an amount of 0.7 mass % or less.

[17] The oral composition of the above [1] to [16], wherein a surfactant other than a component (D), an anionic surfactant, and an amphoteric surfactant is preferably contained in an amount of 0.5 mass or less, more preferably in an amount of 0.1 mass or less, and the surfactant other than a component (D), an anionic surfactant, and an amphoteric surfactant is even more preferably not contained unless otherwise inevitably mixed in.

[18] The oral composition of the above [1] to [17], wherein the oral composition is preferably a liquid oral composition, and more preferably a mouthwash, a liquid toothpaste, a toothwash, a mouth spray, or a gargle.

[19] The oral composition of the above [1] to [18] for use in inhibiting plaque accumulation.

[20] The oral composition of the above [1] to [18] for use in inhibiting halitosis.

[21] The oral composition of the above [1] to [18] for use in inhibition or prevention of dental caries.

[22] Use of the oral composition of the above [1] to [18] for inhibiting plaque accumulation.

[23] Use of the oral composition of the above [1] to [18] for inhibiting halitosis.

[24] Use of the oral composition of the above [1] to [18] for inhibiting or preventing a dental caries.

EXAMPLE

Hereinbelow, the present invention will be specifically described with reference to Examples. Note that in Tables, the content of each component is expressed in mass unless otherwise specified.

[Production Example 1] Production of α,β-Lauryl Galactoside

D-Galactose and lauryl alcohol were reacted in the presence of a catalytic amount of paratoluenesulfonic acid monohydrate while dehydrating under conditions of heating and reduced pressure. The obtained mixture was purified using a silica gel column to obtain lauryl galactoside having a degree of condensation of galactose of 1 to 3. Results of gel permeation chromatography, gas chromatography, and 1H-NMR analysis revealed that the average degree of condensation of galactose in the obtained lauryl galactoside was 1.48 and the composition of lauryl monogalactoside in the component was pyranoside/furanoside=83/17, and the α/β ratio of the pyranoside was 75/25. This was used as α,β-lauryl galactoside.

[Production Example 2] Production of α,β-Octyl Galactoside

α,β-Octyl galactoside was produced using octyl alcohol as a raw material in the same manner as in Production Example 1.

[Production Example 3] Production of α,β-2-Ethylhexyl Galactoside

D-Galactose and 2-ethylhexanol were reacted in the presence of a catalytic amount of paratoluenesulfonic acid monohydrate while dehydrating under conditions of heating and reduced pressure. After reaction, an aqueous solution of sodium hydroxide was added to neutralize the catalyst, and unreacted D-galactose was removed by filtration from the obtained mixture. Unreacted alcohol was distilled off under reduced pressure from the filtrate to obtain 2-ethylhexyl galactoside. Results of gel permeation chromatography, gas chromatography, and $^1$H-NMR analysis revealed that the average degree of condensation of galactose in the obtained 2-ethylhexyl galactoside was 1.16 and the composition of monogalactoside in the composition was pyranoside/furanoside=40/60, and the α/β ratio of the pyranoside was 70/30. This was used as α,β-2-ethylhexyl galactoside.

[Production Example 4] Production of α,β-Decyl Galactoside

Decyl galactoside was obtained by following Production Example 3 except that 2-ethylhexanol used in Production Example 3 was replaced with a decanol isomer mixture (decanol, Kyowa Hakko Chemical Co., Ltd.). The average degree of condensation of galactose in the obtained decyl galactoside was 1.17 and the composition of monogalactoside in the composition was pyranoside/furanoside=46/54, and the α/β ratio of the pyranoside was 67/33. This was used as α,β-decyl galactoside.

[Production Example 5] Production of Isodecyl Galactoside

Isodecyl galactoside was obtained by following Production Example 3 except that 2-ethylhexanol used in Production Example 3 was replaced with isodecanol (Kyowa Hakko Chemical Co., Ltd.). The average degree of condensation of galactose in the obtained isodecyl galactose was 1.14. This was used as isodecyl galactose.

Examples 1 to 11 and Comparative Examples 1 to 3

Using the compounds obtained in Production Examples 1 to 5 as the component (A) appropriately, oral compositions were prepared according to the formulations shown in Table 1. Using the obtained oral compositions, the solubility of the component (A) was evaluated according to the method below.

Results are shown in Table 1.

Test Example 1: Evaluation of Solubility

The obtained compositions were visually observed and evaluated according to the following criteria.

A: No separation or insoluble matter of the component (A) was found, and the composition had homogeneous transparency.

B: No separation or insoluble matter of the component (A) was found, but the composition was slightly cloudy.

C: Separation or insoluble matter of the component (A) was found.

Test Example 2: Evaluation of the Amount of Cationic Bactericide Adsorbed onto Teeth A powder of hydroxyapatite (Hap) (Taihei Chemical Industrial Co., Ltd.; hereinafter abbreviated as Hap), which is the main component of tooth enamel, was used as a tooth model. 10 mg of Hap was immersed in 1 mL of each of the compositions shown in Table 1 for 30 seconds, and then washed with 2 mL of ion exchange water. The bactericide adsorbed onto Hap was extracted with the following mobile phase and quantified under the high speed liquid chromatography conditions below to calculate the amount adsorbed.

(Benzethonium Chloride)
Mobile phase: ion exchange water, 35%; acetonitrile, 65%; sodium alkylsulfate, 0.03 mol/L; sodium perchlorate, 0.1 mol/L
Column: ODS column: Superspher 100 (Kanto Kagaku Co., Inc.)
Flow rate: 1 mL/min
Measurement wavelength: 210 nm
Temperature: 40° C.
(Cetylpyridinium Chloride)
Mobile phase: ion exchange water, 25%; methanol, 75%; sodium perchlorate, 0.05 mol/L
Column: CAPCELL PAK (SCX) (Shiseido Co., Ltd.)
Flow rate: 1.2 mL/min Measurement wavelength: 260 nm    Temperature: 40° C.

TABLE 1

|  | Example 1 | Example 2 | Example 3 | Example 4 | Example 5 | Example 6 | Example 7 |
|---|---|---|---|---|---|---|---|
| (A) α,β-Octyl galactoside |  |  |  | 0.1 |  |  |  |
| Isodecyl galactoside | 0.001 | 0.01 | 0.02 |  | 0.5 | 0.75 | 0.88 |
| (B) Cetylpyridinium chloride |  | 0.01 | 0.01 | 0.01 | 0.01 | 0.01 | 0.01 |
| Benzethonium chloride | 0.01 |  |  |  |  |  |  |
| (D) Polyoxyethylene (40EO) hydrogenated castor oil |  |  |  |  |  |  |  |
| Polyglyceryl (10) monomyristate |  |  |  |  |  |  |  |
| Sucrose myristate |  |  |  |  |  |  |  |
| (C) Water | Balance | Balance | Balance | Balance | Balance | Balance | Balance |
| Total |  |  |  |  |  |  |  |
| (A)/(B) | 0.1 | 1 | 2 | 10 | 50 | 75 | 88 |
| Amount adsorbed onto Hap (ng/mgHAp) | 112 | 75 | 113 | 188 | 709 | 746 | 678 |
| Solubility | A | A | A | A | A | A | A |

|  | Example 8 | Example 9 | Example 10 | Example 11 | Comparative Example 1 | Comparative Example 2 | Comparative Example 3 |
|---|---|---|---|---|---|---|---|
| (A) α,β-Octyl galactoside |  |  |  |  |  |  |  |
| Isodecyl galactoside | 1 | 0.1 | 0.1 | 0.1 |  |  | 1.2 |
| (B) Cetylpyridinium chloride | 0.01 | 0.01 | 0.01 | 0.01 |  | 0.01 | 0.01 |
| Benzethonium chloride |  |  |  |  | 0.01 |  |  |
| (D) Polyoxyethylene (40EO) hydrogenated castor oil |  | 0.2 |  |  |  |  |  |
| Polyglyceryl (10) monomyristate |  |  | 0.2 |  |  |  |  |
| Sucrose myristate |  |  |  | 0.2 |  |  |  |
| (C) Water | Balance | Balance | Balance | Balance | Balance | Balance | Balance |
| Total |  |  |  |  |  |  |  |
| (A)/(B) | 100 | 10 | 10 | 10 |  |  | 120 |
| Amount adsorbed onto Hap (ng/mgHAp) | 469 | 126 | 230 | 1714 | 81 | 73 | 699 |
| Solubility | B | A | A | A | A | A | C |

The results shown in Table 1 indicated that in Examples 1 to 11 in which the predetermined amounts of the component (A) and the cationic bactericide were used in combination resulted in enhanced solubility of the component (A) and effectively improved adsorption of the cationic bactericide onto teeth, whereas Comparative Example 1 in which the component (A) was not used, Comparative example 2 in which the cationic bactericide was not used, and Comparative Example 3 in which both of the components were used in combination but the amount of the component (A) exceeded the predetermined amount, resulted in failure to fully provide both the effect of enhancing the solubility of the component (A) and the effect of increasing the adsorption of the cationic bactericide onto teeth.

Examples 12 to 26 and Comparative Examples 4 to 9

Using the compounds obtained in Production Examples 1 to 5 as the component (A) appropriately, oral compositions were prepared according to the formulations shown in Tables 2 to 3. Using the obtained oral compositions, the solubility of the component (A) was evaluated in the same manner as in Test Example 1.

Results are shown in Tables 2 and 3.

TABLE 2

|  | Example 12 | Example 13 | Example 14 | Example 15 | Example 16 | Example 17 | Example 18 | Example 19 |
|---|---|---|---|---|---|---|---|---|
| (A) Isodecyl galactoside | 0.2 |  |  | 0.2 |  |  | 0.2 |  |
| α,β-Octyl galactoside |  | 0.2 |  |  | 0.2 |  |  | 0.2 |
| α,β-Lauryl galactoside |  |  | 0.2 |  |  | 0.2 |  |  |

TABLE 2-continued

|  | Example 12 | Example 13 | Example 14 | Example 15 | Example 16 | Example 17 | Example 18 | Example 19 |
|---|---|---|---|---|---|---|---|---|
| (B) Cetylpyridinium chloride | 0.05 | 0.05 | 0.05 |  |  |  |  |  |
| Benzethonium chloride |  |  |  | 0.05 | 0.05 | 0.05 |  |  |
| Benzalkonium chloride |  |  |  |  |  |  | 0.05 | 0.05 |
| Chlorhexidine gluconate |  |  |  |  |  |  |  |  |
| Chlorhexidine hydrochloride |  |  |  |  |  |  |  |  |
| (C) Water | Balance | Balance | Balance | Balance | Balance | Balance | Balance | Balance |
| Total | 100 | 100 | 100 | 100 | 100 | 100 | 100 | 100 |
| Solubility | A | A | A | A | A | A | A | A |

|  | Example 20 | Example 21 | Example 22 | Example 23 | Example 24 | Example 25 | Example 26 |
|---|---|---|---|---|---|---|---|
| (A) Isodecyl galactoside |  | 0.2 |  |  | 0.2 |  |  |
| α,β-Octyl galactoside |  |  | 0.2 |  |  | 0.2 |  |
| α,β-Lauryl galactoside | 0.2 |  |  | 0.2 |  |  | 0.2 |
| (B) Cetylpyridinium chloride |  |  |  |  |  |  |  |
| Benzethonium chloride |  |  |  |  |  |  |  |
| Benzalkonium chloride | 0.05 |  |  |  |  |  |  |
| Chlorhexidine gluconate |  | 0.05 | 0.05 | 0.05 |  |  |  |
| Chlorhexidine hydrochloride |  |  |  |  | 0.05 | 0.05 | 0.05 |
| (C) Water | Balance | Balance | Balance | Balance | Balance | Balance | Balance |
| Total | 100 | 100 | 100 | 100 | 100 | 100 | 100 |
| Solubility | A | A | A | A | A | A | A |

TABLE 3

|  | Comparative Example 4 | Comparative Example 5 | Comparative Example 6 | Comparative Example 7 | Comparative Example 8 | Comparative Example 9 |
|---|---|---|---|---|---|---|
| (A) Isodecyl galactoside | 0.2 |  |  | 0.2 |  |  |
| α,β-Octyl galactoside |  | 0.2 |  |  | 0.2 |  |
| α,β-Lauryl galactoside |  |  | 0.2 |  |  | 0.2 |
| Triclosan | 0.05 | 0.05 | 0.05 |  |  |  |
| Isopropylmethylphenol |  |  |  | 0.05 | 0.05 | 0.05 |
| (C) Water | Balance | Balance | Balance | Balance | Balance | Balance |
| Total | 100 | 100 | 100 | 100 | 100 | 100 |
| Solubility | C | C | C | C | C | C |

The results shown in Tables 2 and 3 revealed that Examples 12 to 26 in which the cationic bactericide was used in the predetermined amount resulted in an excellent solubility of the component (A), whereas Comparative Examples 4 to 9 in which a nonionic bactericide was used instead of the cationic bactericide resulted in failure to dissolve the component (A).

Examples 27 to 50 and Comparative Examples 10 to 16

Using the compounds obtained in Production Examples 1 to 5 as the component (A) appropriately, oral compositions were prepared according to the formulations shown in Tables 4 to 6. Using the obtained oral compositions, the solubility of the component (A) was evaluated in the same manner as in Test Example 1 and the coaggregation-inhibiting effect was also evaluated according to the method below.

Results are shown in Tables 4 to 6.

Text Example 3: Evaluation of Coaggregation-Inhibiting Effect (1) Bacterial Strains Used

*Fusobacterium nucleatum* strain F-1 (hereinafter referred to as F-1 bacterium) was used as the bacterium belonging to the genus *Fusobacterium*. *Streptococcus sobrinus* strain B13 (hereinafter Ss bacterium), which is a dental caries pathogen, was used as the bacterium to be subjected to the coaggregation reaction.

(2) Coaggregation Measurement Method

Ss bacterium was inoculated in brain heart infusion liquid medium and then cultured for 20 hours at 37° C. under anaerobic conditions. F-1 bacterium was inoculated in GAM broth liquid medium and then cultured for 20 hours at 37° C. under anaerobic conditions. After completion of the culturing, bacteria were collected by centrifugation and washed twice with a pH 8.0 buffer solution for coaggregation (1 mM tris(hydroxymethyl)aminomethane, 0.1 mM calcium chloride, 0.1 mM magnesium chloride, and 0.15 M sodium chloride). After washing, using the buffer solution for coaggregation, F-1 bacterium was adjusted to have a turbidity (OD: UV-1600, UV-Visible spectrophotometer (Shimadzu Corporation)) of 0.25, and Ss cell was adjusted to have a turbidity of 0.9, both at a wavelength of 600 nm, to obtain bacterial suspensions. The buffer solution for coaggregation was used instead of water as the component (C) shown in Tables 3 to 5. In the test, a round bottom 96-well microplate (Thai Polypropylene Co., Ltd.) was used, and 100 µL of any of the F-1 bacterial suspension, 50 µL of the Ss bacterial suspension, and 50 µL of the oral composition shown in Tables 3 to 5 were successively admixed. The admixture was left to stand at room temperature for a whole day and night, and then the mixture in which no precipitation of aggregate was found was evaluated as having the coaggregation-inhibiting effect (+), whereas the mixture in which precipitation of aggregate was found was evaluated as not having the coaggregation-inhibiting effect (−).

TABLE 4

|  |  | Example 27 | Example 28 | Example 29 | Example 30 | Example 31 | Example 32 |
|---|---|---|---|---|---|---|---|
| (A) | Isodecyl galactoside | 0.05 | 0.2 | 0.05 | 0.1 | 0.05 | 0.1 |
| (B) | Cetylpyridinium chloride | 0.05 | 0.05 | 0.02 | 0.02 | 0.02 | 0.02 |
|  | Benzethonium chloride |  |  |  |  |  |  |
| (D) | Polyoxyethylene (40) hydrogenated castor oil | 0.5 | 0.5 | 0.5 | 0.5 | 0.6 | 0.6 |
| (C) | Water | Balance | Balance | Balance | Balance | Balance | Balance |
|  | Total | 100 | 100 | 100 | 100 | 100 | 100 |
|  | (A)/(B) | 1 | 4 | 2.5 | 5 | 2.5 | 5 |
|  | {(A) + (B)}/(D) | 0.20 | 0.50 | 0.14 | 0.24 | 0.12 | 0.20 |
|  | Solubility | A | A | A | A | A | A |
|  | Coaggregation-inhibiting effect | + | + | + | + | + | + |

|  |  | Example 33 | Example 34 | Example 35 | Example 36 | Example 37 | Example 38 |
|---|---|---|---|---|---|---|---|
| (A) | Isodecyl galactoside | 0.05 | 0.2 | 0.05 | 0.1 | 0.05 | 0.2 |
| (B) | Cetylpyridinium chloride | 0.01 | 0.01 | 0.01 | 0.01 |  |  |
|  | Benzethonium chloride |  |  |  |  | 0.01 | 0.01 |
| (D) | Polyoxyethylene (40) hydrogenated castor oil | 0.5 | 0.5 | 1 | 1 | 0.5 | 0.5 |
| (C) | Water | Balance | Balance | Balance | Balance | Balance | Balance |
|  | Total | 100 | 100 | 100 | 100 | 100 | 100 |
|  | (A)/(B) | 5 | 20 | 5 | 10 | 5 | 20 |
|  | {(A) + (B)}/(D) | 0.12 | 0.42 | 0.06 | 0.11 | 0.12 | 0.42 |
|  | Solubility | A | A | A | A | A | A |
|  | Coaggregation-inhibiting effect | + | + | + | + | + | + |

TABLE 5

|  |  | Example 39 | Example 40 | Example 41 | Example 42 | Example 43 | Example 44 |
|---|---|---|---|---|---|---|---|
| (A) | Isodecyl galactoside | 0.05 | 0.2 | 0.05 | 0.1 | 0.05 | 0.1 |
|  | 2-Ethylhexyl galactoside |  |  |  |  |  |  |
|  | α,β-Octyl galactoside |  |  |  |  |  |  |
|  | α,β-Decyl galactoside |  |  |  |  |  |  |
|  | α,β-Lauryl galactoside |  |  |  |  |  |  |
| (B) | Cetylpyridinium chloride |  |  | 0.01 | 0.01 | 0.01 | 0.01 |
|  | Benzalkonium chloride | 0.01 | 0.01 |  |  |  |  |
| (D) | Polyoxyethylene (40) hydrogenated castor | 0.5 | 0.5 |  |  |  |  |
|  | Polyoxyethylene sorbitan monostearate |  |  | 0.5 |  |  |  |
|  | Polyglyceryl (10) monolaurate |  |  |  | 0.5 |  |  |
|  | Polyoxyethylene (23) lauryl ether |  |  |  |  | 0.5 |  |
|  | Decyl glucoside |  |  |  |  |  | 0.5 |
| (C) | Water | Balance | Balance | Balance | Balance | Balance | Balance |
|  | Total | 100 | 100 | 100 | 100 | 100 | 100 |
|  | (A)/(B) | 5 | 20 | 20 | 10 | 5 | 10 |

TABLE 5-continued

|  | | | | | | |
|---|---|---|---|---|---|---|
| {(A) + (B)}/(D) | 0.12 | 0.42 | 0.42 | 0.22 | 0.12 | 0.22 |
| Solubility | A | A | A | A | A | A |
| Coaggregation-inhibiting effect | + | + | + | + | + | + |

|  | | Example 45 | Example 46 | Example 47 | Example 48 | Example 49 | Example 50 |
|---|---|---|---|---|---|---|---|
| (A) | Isodecyl galactoside | | | | | | |
|  | 2-Ethylhexyl galactoside | 0.05 | 0.2 | | | | |
|  | α,β-Octyl galactoside | | | 0.05 | | | |
|  | α,β-Decyl galactoside | | | | 0.1 | | |
|  | α,β-Lauryl galactoside | | | | | 0.05 | 0.2 |
| (B) | Cetylpyridinium chloride | 0.01 | 0.01 | 0.01 | 0.01 | 0.01 | 0.01 |
|  | Benzalkonium chloride | | | | | | |
| (D) | Polyoxyethylene (40) hydrogenated castor | 0.5 | 0.5 | 0.5 | 0.5 | 0.5 | 0.5 |
|  | Polyoxyethylene sorbitan monostearate | | | | | | |
|  | Polyglyceryl (10) monolaurate | | | | | | |
|  | Polyoxyethylene (23) lauryl ether | | | | | | |
|  | Decyl glucoside | | | | | | |
| (C) | Water | Balance | Balance | Balance | Balance | Balance | Balance |
|  | Total | 100 | 100 | 100 | 100 | 100 | 100 |
|  | (A)/(B) | 5 | 20 | 5 | 10 | 5 | 20 |
|  | {(A) + (B)}/(D) | 0.12 | 0.42 | 0.12 | 0.22 | 0.12 | 0.42 |
|  | Solubility | A | A | A | A | A | A |
|  | Coaggregation-inhibiting effect | + | + | + | + | + | + |

TABLE 6

|  | | Comparative Example 10 | Comparative Example 11 | Comparative Example 12 | Comparative Example 13 | Comparative Example 14 | Comparative Example 15 | Comparative Example 16 |
|---|---|---|---|---|---|---|---|---|
| (A) | α,β-Lauryl galactoside | 0.8 | 0.8 | 0.8 | 0.8 | 0.8 | 0.8 | 0.8 |
| (D) | Polyoxyethylene (25) hydrogenated castor oil | 2 | | | | | | |
|  | Polyoxyethylene (40) hydrogenated castor oil | | 2 | | | | | |
|  | Polyoxyethylene (60) hydrogenated castor oil | | | 2 | | | | |
|  | Polyoxyethylene (80) hydrogenated castor oil | | | | 2 | | | |
|  | Polyoxyethylene (20) sorbitan cocoate | | | | | 2 | | |
|  | Polyoxyethylene (20) sorbitan monopalmitate | | | | | | 2 | |
|  | Polyoxyethylene (20) sorbitan monooleate | | | | | | | 2 |
| (C) | Water | Balance | Balance | Balance | Balance | Balance | Balance | Balance |
|  | Total | 100 | 100 | 100 | 100 | 100 | 100 | 100 |
|  | Solubility | A | A | A | A | A | A | A |
|  | Coaggregation-inhibiting effect | − | − | − | − | − | − | − |

The results shown in Tables 4 to 6 revealed that Comparative Examples 10 to 16 in which an excessive amount of the nonionic surfactant was contained as the component (D) to dissolve the component (A) resulted in inactivation of coaggregation-inhibiting effect, whereas Examples 27 to 50 in which the solubility of the component (A) was enhanced by the combined use of the component (A) and the predetermined amount of the cationic bactericide as the component (B), resulted in reduction of the content of the nonionic surfactant of the component (D), consequently exhibiting a good coaggregation-inhibiting effect.

Example 51

The following mouthwash or liquid toothpaste was obtained as a liquid composition.

| Mouthwash, liquid toothpaste | (mass %) |
|---|---|
| Cetylpyridinium chloride | 0.01 |
| Isodecyl galactoside | 0.1 |
| Polyoxyethylene (40 E.O.) hydrogenated castor oil | 0.8 |
| Sorbitol | 10.0 |
| Sodium saccharin | 0.01 |
| Ethyl parahydroxybenzoate | 0.1 |
| Fragrance | 0.2 |
| Purified water | Balance |

What is claimed is:

1. An oral composition comprising the following components (A), (B), (C) and (D):

(A) 0.01 mass % to 0.5 mass % of a compound represented by the following formula (I):

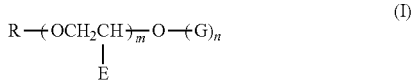

wherein R represents an optionally substituted linear or branched alkyl group having 8 to 18 carbon atoms, G represents a galactose residue, E represents a hydrogen atom or a methyl group, m is 0, and n represents an integer of 1 to 3;
- (B) 0.001 mass % to 0.1 mass % of a cationic bactericide selected from the group consisting of cetylpyridinium chloride, benzethonium chloride, benzalkonium chloride, chlorhexidine gluconate and chlorhexidine hydrochloride;
- (C) 35 mass % or more of water; and
- (D) 0.1 mass % to 1.5 mass % of a nonionic surfactant, wherein, in the oral composition, the solubility of the compound represented by formula (I) is enhanced as compared to its solubility in a second composition that is the same as the oral composition except that the second composition lacks component (B), the cationic bactericide and wherein (A)/(B), the mass ratio of the content of component (A) to the content of component (B), is 0.1 to 100.

2. The oral composition according to claim 1, comprising 0.2 to 1.2 mass % of component (D).

3. The oral composition according to claim 1, wherein (A)/(B), the mass ratio of the content of component (A) to the content of component (B), is 2 to 100.

4. The oral composition according to claim 2, wherein {(A)+(B)}/(D), the mass ratio of the total content of component (A) and component (B) to the content of component (D), is 0.02 to 2.

5. The oral composition according to claim 1, wherein the composition comprises 0.008 mass % to 0.06 mass % of component (B).

6. The oral composition according to claim 2, wherein component (D) is one or two or more selected from the group consisting of a polyoxyethylene hydrogenated castor oil, a polyoxyethylene sorbitan fatty acid ester, a polyglycerol fatty acid ester, a polyoxyethylene alkyl ether, an alkyl polyglucoside, and a sucrose fatty acid ester.

7. The oral composition according to claim 1, wherein the oral composition is a liquid oral composition.

8. A method for inhibiting plaque accumulation, comprising applying, to the oral cavity, an oral composition comprising the following components (A), (B), (C) and (D):
- (A) 0.01 mass % to 0.5 mass % of a compound represented by the following formula (I):

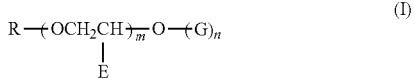

wherein R represents an optionally substituted linear or branched alkyl group having 8 to 18 carbon atoms, G represents a galactose residue, E represents a hydrogen atom or a methyl group, m is 0, and n represents an integer of 1 to 3;
- (B) 0.001 mass % to 0.1 mass % of a cationic bactericide selected from the group consisting of cetylpyridinium chloride, benzethonium chloride, benzalkonium chloride, chlorhexidine gluconate and chlorhexidine hydrochloride;
- (C) 35 mass % or more of water; and
- (D) 0.1 mass % to 1.5 mass % of a nonionic surfactant, wherein, in the oral composition, the solubility of the compound represented by formula (I) is enhanced as compared to its solubility in a second composition that is the same as the oral composition except that the second composition lacks component (B), the cationic bactericide, and wherein (A)/(B), the mass ratio of the content of component (A) to the content of component (B), is 0.1 to 100.

9. A method for inhibiting halitosis, comprising applying, to the oral cavity, an oral composition comprising the following components (A), (B), (C) and (D):
- (A) 0.01 mass % to 0.5 mass % of a compound represented by the following formula (I):

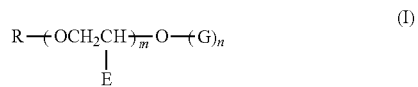

wherein R represents an optionally substituted linear or branched alkyl group having 8 to 18 carbon atoms, G represents a galactose residue, E represents a hydrogen atom or a methyl group, m is 0, and n represents an integer of 1 to 3;
- (B) 0.001 mass % to 0.1 mass % of a cationic bactericide selected from the group consisting of cetylpyridinium chloride, benzethonium chloride, benzalkonium chloride, chlorhexidine gluconate and chlorhexidine hydrochloride; and
- (C) 35 mass % or more of water; and
- (D) 0.1 mass % to 1.5 mass % of a nonionic surfactant, wherein, in the oral composition, the solubility of the compound represented by formula (I) is enhanced as compared to its solubility in a second composition that is the same as the oral composition except that the second composition lacks component (B), the cationic bactericide, and wherein (A)/(B), the mass ratio of the content of component (A) to the content of component (B), is 0.1 to 100.

10. The method according to claim 8, wherein the composition comprises 0.2 mass % to 1.2 mass % of component (D).

11. The method according to claim 8, wherein the composition comprises 0.2 mass % to 1.2 mass % of component (D).

* * * * *